US008629184B2

(12) United States Patent
Wolicki et al.

(10) Patent No.: US 8,629,184 B2
(45) Date of Patent: Jan. 14, 2014

(54) TOPICAL FORMULATIONS FOR TREATMENT OF NEUROPATHY

(75) Inventors: Richard Wolicki, Imperial Beach, CA (US); Stanley Kim, San Diego, CA (US)

(73) Assignee: TARAXOS, Inc., San Diego, CA (US)

( * ) Notice: Subject to any disclaimer, the term of this patent is extended or adjusted under 35 U.S.C. 154(b) by 231 days.

(21) Appl. No.: 13/120,894

(22) PCT Filed: Sep. 25, 2009

(86) PCT No.: PCT/US2009/058446
§ 371 (c)(1),
(2), (4) Date: Mar. 24, 2011

(87) PCT Pub. No.: WO2010/036937
PCT Pub. Date: Apr. 1, 2010

(65) Prior Publication Data
US 2011/0178177 A1    Jul. 21, 2011

Related U.S. Application Data

(60) Provisional application No. 61/100,711, filed on Sep. 27, 2008.

(51) Int. Cl.
*A01N 37/12* (2006.01)
*A01N 37/44* (2006.01)
*A01N 33/02* (2006.01)
*A61K 31/195* (2006.01)
*A61K 31/135* (2006.01)
*A61K 9/00* (2006.01)

(52) U.S. Cl.
USPC ............................ 514/561; 514/647; 424/400

(58) Field of Classification Search
USPC .................................. 514/561, 647; 424/400
See application file for complete search history.

(56) References Cited

U.S. PATENT DOCUMENTS

| | | | |
|---|---|---|---|
| 6,147,102 A | 11/2000 | Borgman | |
| 6,166,085 A | 12/2000 | Chaplan et al. | |
| 6,248,789 B1 * | 6/2001 | Weg | 514/647 |
| 6,290,986 B1 | 9/2001 | Murdock et al. | |
| 6,376,530 B1 | 4/2002 | Claiborne et al. | |
| 6,406,716 B2 * | 6/2002 | Caruso et al. | 424/468 |
| 6,596,900 B2 | 7/2003 | Blackemore et al. | |
| 6,689,399 B1 | 2/2004 | Dickson | |
| 6,730,667 B2 | 5/2004 | Deagle | |
| 6,770,661 B2 | 8/2004 | Shao et al. | |
| 7,687,080 B2 | 3/2010 | Wolicki | |
| 2002/0028789 A1 | 3/2002 | Ford | |
| 2002/0115705 A1 * | 8/2002 | Magnus-Miller et al. | 514/403 |
| 2003/0100931 A1 | 5/2003 | Mullett | |
| 2004/0058313 A1 * | 3/2004 | Abreu | 435/5 |
| 2004/0101582 A1 | 5/2004 | Wolicki | |
| 2007/0225257 A1 | 9/2007 | Baudy | |
| 2010/0184817 A1 | 7/2010 | Wolicki | |

FOREIGN PATENT DOCUMENTS

| | | |
|---|---|---|
| DE | 1998-494827 | 9/1998 |
| EP | 1048294 A2 | 11/2000 |
| WO | WO 97/10815 | 3/1997 |
| WO | WO 9720551 A1 | 6/1997 |
| WO | WO 0101983 A1 | 1/2001 |

OTHER PUBLICATIONS

International Search Report and Written Opinion for PCT/US09/58446 filed Sep. 25, 2009.
Felsby et al., NMDA receptor blockage in chronic neuropathic pain: a comparison of ketakmein and magnesim chloride; Pain, 64 (1995) pp. 283-291.
Warncke et al., Ketamine, an NMDA receptor antagonist, suppresses spatial and temporal properties of burn-induced secondary hyperalgesia in man: a double blind, cross-over comparison with morphine and placebo; Pain, 72 (1997): pp. 99-106.
Padilla et al., Topical medications for orofacial neuropathic pain: a review: JADA, vol. 131, Feb. 2000; pp. 184-195.
Marty's Algorithm for Chronic Neuropathy, Sep. 1999, Modified Mar. 2000.
Extended European Search Report in EP 09816933.7, issued Mar. 30, 2012.

* cited by examiner

*Primary Examiner* — Sreeni Padmanabhan
*Assistant Examiner* — Uma Ramachandran
(74) *Attorney, Agent, or Firm* — Knobbe, Martens, Olson & Bear LLP

(57) ABSTRACT

Topical treatments for neuropathy are described. The treatments include topical formulations of NMDA antagonists and one additional active ingredient. In one example, the formulation includes ketamine and gabapentin for the treatment of a subject's neuropathy. These transdermal or topical compositions provide a surprising degree of effective relief from the symptoms of peripheral neuropathy and can be administered to subjects to treat various neuropathies.

15 Claims, No Drawings

TOPICAL FORMULATIONS FOR TREATMENT OF NEUROPATHY

RELATED APPLICATIONS

This application is the U.S. National Phase under 35 U.S.C. of §371 of International PCT application number PCT/US2009/058446, filed Sep. 25, 2009 in the English language, which claims the benefit of U.S. Provisional Application Ser. No. 61/100,711, filed Sep. 27, 2008, the contents of which are hereby incorporated by reference in their entirety.

BACKGROUND OF THE INVENTION

1. Field of the Invention

The present invention relates to methods and compositions for the topical treatment of neuropathy. More particularly, the present invention relates to topical compositions including a combination of ingredients that provides a surprising degree of effective relief from the symptoms of neuropathy with minimal side effects and to methods for administering topical compositions to treat neuropathy. Preferred embodiments contemplate chemical, biological or physical means of reducing such side effects.

2. Description of the Related Art

Peripheral neuropathy is a condition involving nerve-end damage anywhere in the body. Peripheral neuropathy generally refers to a disorder that affects the peripheral nerves, most often manifested as one or a combination of motor, sensory, sensorimotor, or autonomic neural dysfunction. The wide variety of morphologies exhibited by peripheral neuropathies can each be uniquely attributed to an equally wide variety of causes. For instance, peripheral neuropathies can be genetically acquired, can result from a systemic disease, can manifest as a post-surgical complication, or can be induced by a toxic agent. Some toxic agents that cause neurotoxicities are therapeutic drugs, antineoplastic agents, contaminants in foods or medicinals, and environmental and industrial pollutants. As much as 3% of the population is estimated to be affected, if not greater.

Although a number of neuropathies are related to the disease diabetes mellitus, others, although not known to be related to diabetes are similar in their physiological effects on the peripheral vascular system. Such diseases include Raynaud's Phenomenon, including CREST syndrome, autoimmune diseases such as erythromatosis, and rheumatoid diseases. Other peripheral neuropathies include the following: HIV-associated neuropathy; nutritional deficiency-associated neuropathy; cranial nerve palsies; drug-induced neuropathy; industrial neuropathy; lymphomatous neuropathy; myelomatous neuropathy; multi-focal motor neuropathy; immune-mediated disorders, chronic idiopathic sensory neuropathy; carcinomatous neuropathy; acute pain autonomic neuropathy; alcoholic neuropathy; compressive neuropathy; vasculitic/ischaemic neuropathy; mono- and poly-neuropathies.

For example, among the most important toxic agents causing peripheral neuropathy are therapeutic agents, particularly those used for the treatment of neoplastic disease. In certain cases, peripheral neuropathy is a major complication of cancer treatment and is the main factor limiting the dosage of chemotherapeutic agents that can be administered to a patient (Macdonald, Neurologic Clinics 9:955-967 (1991)). This is true for the commonly administered agents cisplatin, paclitaxel and vincristine (Broun, et al., Am. J. Clin. Oncol. 16:18-21 (1993); Macdonald, Neurologic Clinics 9:955-967 (1991); Casey, et al., Brain 96:69-86 (1973)). The identification of methods for preventing or alleviating dose-limiting peripheral neuropathologic side effects would allow higher, and more therapeutically effective doses of these chemotherapeutics to be administered to patients, i.e., the therapeutic efficacy of such chemotherapeutics is typically a function of dose and therefore, increasing dosage provides increased patient survival (Macdonald, Neurologic Clinics 9:955-967 (1991); Oxols, Seminars in Oncology 16, suppl. 6:22-30 (1989))

The N-methyl-D-aspartate (NMDA) receptor seems to play a major role in neuropathic pain and in the development of opioid tolerance. Experiments in both animals and humans have established that NMDA antagonists such as ketamine and dextromethorphan can alleviate neuropathic pain and reverse opioid tolerance. Unfortunately, only a few NMDA antagonists are clinically available and their use is limited by unacceptable side effects.

Generally, depressed NMDA receptor function is associated with an array of negative symptoms. They sometimes induce "psychotomimetic" side effects, symptoms resembling psychosis. Such side effects caused by NMDA receptor inhibitors can include hallucinations, paranoid delusions, confusion, difficulty concentrating, agitation, convulsions, alterations in mood, nightmares (Muir, K W; Lees K R (1995), and may exhibit personality changes and disorganized thinking. "Clinical experience with excitatory amino acid antagonist drugs". Stroke 26 (3): 503-513.) catatonia (Aarts, M M; Tymianski M (2003). "Novel treatment of excitotoxicity: targeted disruption of intracellular signalling from glutamate receptors". Biochemical Pharmacology 66 (6): 877-886.) ataxia (Kim A H, Kerchner G A, and Choi D W. (2002). "Blocking Excitotoxicity". In CNS Neuroproteciton. Marcoux F W and Choi D W, editors. Springer, New York. Pages 3-36), anaesthesia (Kristensen, J D; Svensson B, and Gordh T Jr (1992). "The NMDA-receptor antagonist CPP abolishes neurogenic 'wind-up pain' after intrathecal administration in humans". Pain 51 (2): 249-253. PMID 1484720.) and learning and memory deficits (Rockstroh, S; Emre M, Tarral A, and Pokorny R (1996). "Effects of the novel NMDA-receptor antagonist SDZ EAA 494 on memory and attention in humans". Psychopharmacology 124 (3): 261-266.) In certain animals, such as rats, certain NMDA antagonists cause neurotoxicity and permanent brain injury (see, e.g., Olney J, Labruyerre J and Price M T. 1989. Pathological changes induced in cerebrocortical neurons by phencyclidine and related drugs. Science, Volume 244, Issue 4910, Pages 1360-1362; Ellison G. 1995. The N-methyl-D-aspartate antagonists phencyclidine, ketamine and dizocilpine as both behavioral and anatomical models of the dementias. Brain Research. Brain Research Reviews, Volume 20, Issue 2, Pages 250-267).

The use of ketamine transdermally in an organogel has shown some promise in the treatment of neuropathy. Because ketamine is an N-methyl-D-aspartate receptor antagonist it blocks a cascade of intracellular events that inhibit the hyper excitability of spinal cord neurons. Animal data show that certain spontaneous pains and allodynia have been treated successfully with Ketamine. Also, in humans, phantom limb pain has been treated with some success (Nadine & Bouhassira, Acta. Neurol. Scand 1999 (Supp 173):12-24). Ketamine has been used experimentally to treat neuropathic pain by a variety of routes including the intravenous and subcutaneous. A topical form of low doses of Ketamine has shown some efficacy in treating painful neuropathy when other traditional medicines have failed. (Crowley et al., International Journal of Pharmaceutical Compounding 1998; 2:122-1273).

Other compositions have been employed, including combinations of individual compounds. U.S. Pat. No. 6,387,957

(Frome) relates to the treatment of Sympathetically Mediated Pain (SMP), which include various neuropathies, employing the compounds ketamine (NMDA receptor antagonist), amitriptyline (antidepressant), and guanethidine (sympathetic blocking agent), in combination or independently. U.S. Patent Publication Nos. 2004/0204366 and 2004/0101582 attack the problem with a spectrum of analgesic compounds including combinations of ketamine, gabapentin and clonodine. Other solutions have attempted to increase the absorption of the compounds, see, e.g., US Patent Publication. No. 2004/0076648. Each of these references is incorporated herein by reference.

PCT Publication WO 9807447 describes combinations of anti-epileptic compounds, including gabapentin, with NMDA receptor antagonists. PCT Publications WO 9912537 and WO 0053225 describe combinations of NMDA antagonists and GABA analogs, including gabapentin and pregabalin. PC Publication WO 0200434 describes the use of NMDA antagonists in the treatment of central neuropathic pain. PCT Publication WO 05102390 describes alpha-2-delta ligands in combination with NMDA antagonists as analgesics.

PCT Publication WO 03061656 describes a composition for treating disorders of the central nervous system comprising a GABA analog, such as gabapentin or pregabalin, with an NMDA receptor antagonist such as dextromethomorphan or d-methadone, optionally in combination with another pharmaceutically active substance.

PC Publications WO 9912537 and WO 0053225 describe combinations of anti-epileptic compounds, including gabapentin and pregabalin, in combination with NMDA antagonists as analgesics.

PC Publication WO 03091241 describes NR2B antagonists for a number of indications, together with alpha-2-delta ligands, e.g. gabapentin and pregabalin.

Accordingly, there remains a need in the art for effective treatments for neuropathies, and other neuropathic pains.

SUMMARY OF THE INVENTION

In one aspect, the compositions described herein can provide for the treatment of peripheral neuropathy, and can include a therapeutically effective amount of at least one NMDA antagonist and one additional active compound in a pharmaceutically acceptable diluent or carrier suitable for topical or transdermal use. In one embodiment, the NMDA antagonist is provided in relatively high concentrations, such as greater than 15% by weight. NMDA antagonists may include, but are not limited to, PCP, nitrous oxide, ketamine, MK-801, methadone, dextropropoxyphene, and ketobemidone.

In other aspects, methods described herein are directed to treating peripheral neuropathy, comprising the step of transdermal or topical administration of an effective amount of a pharmaceutical composition as described herein to the affected area of a subject in need of such treatment. Other drugs or ingredients may be added as needed to increase the analgesic effect or minimize the side effects.

In other embodiments, the peripheral neuropathy is a diabetic neuropathy. It will be clearly understood that the diabetic neuropathy may be associated with Type 1 (insulin-dependent) diabetes, Type 2 (non-insulin-dependent) diabetes, or both.

In some embodiments, the neuropathy is a non-diabetic neuropathy. Such a non-diabetic neuropathy may be genetically acquired, such as Charcot-Marie-Tooth syndrome. In other embodiments the peripheral neuropathy can result from a systemic or infectious disease such as HIV, or an infectious disease condition such as AIDS. In further embodiments, the peripheral neuropathy manifests as a post surgical complication.

In other embodiments the peripheral neuropathy is induced by a toxic agent. For example, the peripheral neuropathy can be caused by a chemotherapeutic agent such as paclitaxel (or other taxane derivative), vincristine, cisplatin, an agent used for the treatment of infectious diseases such as streptomycin, didanosine or zalcitabine, or any other chemically toxic agent. Infectious disease conditions such as post-polio syndrome or AIDS-associated neuropathy are specifically contemplated.

Other peripheral neuropathies include the following: HIV associated neuropathy; B12-deficiency associated neuropathy; cranial nerve palsies; drug-induced neuropathy; industrial neuropathy; lymphomatous neuropathy; myelomatous neuropathy; multi-focal motor neuropathy; chronic idiopathic sensory neuropathy; carcinomatous neuropathy; acute pan autonomic neuropathy; alcoholic neuropathy; compressive neuropathy; vasculitic/ischaemic neuropathy; mono- and poly-neuropathies.

In further embodiments, the neuropathy is due to low back pain, Guillain-Barre Syndrome, sciatica, or other chronic pain.

Further embodiments include methods for treating a subject suffering from peripheral neuropathy, the methods comprising topically administering an effective amount of the composition consisting essentially of ketamine and gabapentin formulated in a pharmaceutically acceptable topical carrier.

In an alternate embodiment, the methods comprise topically administering an effective amount of a composition comprising a NMDA antagonist formulated in a pharmaceutically acceptable carrier for topical treatment.

The compositions described herein can be administered in therapeutically effective amounts. A therapeutically effective amount means the amount required to at least partly to attain the desired effect, e.g., to effectively alleviate or prevent the symptoms of the peripheral neuropathy or pain, to mitigate the side effects of certain compounds such as neurotoxicity or psychosis or drowsiness, to effectuate or potentiate the activity of the invention composition, or combinations thereof.

DETAILED DESCRIPTION OF THE INVENTION

In one aspect, the pharmaceutical compositions described herein can be used for the treatment of peripheral neuropathy. These compositions can include therapeutically effective amounts of at least one NMDA (receptor) antagonist and one additional active ingredient, such as gabapentin or clonidine which limits or mitigates the side effects of the NMDA (receptor) antagonist. In this embodiment the composition is formulated in a pharmaceutically acceptable diluent or carrier suitable for transdermal or topical use. Surprisingly, it was found that only one additional active ingredient was necessary to counteract the potential side affects of the NMDA (receptor) antagonist. Prior compositions used a plurality additional ingredients to counter the side effects of NMDA (receptor) antagonists. For example, prior compositions included ketamine, clonidine and gabapentin (See U.S. Publication 2004-0101582A1).

In one embodiment, the composition consists essentially of ketamine and gabapentin to treat neuropathy when the composition is administered topically in a physiologically acceptable vehicle. In one embodiment, the composition consists essentially of at least about 15% or 20% or more ketamine and at least about 3% gabapentin.

As used herein, the treatment of neuropathy refers to an anti-neuropathic response or a pain-reducing response elicited through the synergistic effect of the two compositions within each formulation as described herein, in which the combined effect of the two agents effectively mitigates, relieves, alleviates, reduces or removes the symptoms of peripheral neuropathy, provides a beneficial effect to the subject; and/or effectively mitigates or reduces the side effects associated with the NMDA-receptor antagonist. The compositions described herein may provide one or more of the following beneficial effects to a patient when topically applied in effective amounts: relief of pain, burning, tingling, electrical sensations and/or hyperalgesia. Also increased microcirculation, nitric oxide stabilization, and facilitated healing of skin ulcers and lesions. Additionally, protein kinase C inhibition, decreased oxidative stress, anti-inflammation, protection against radiation damage (particularly ultraviolet radiation), blockage of the formation of leukotrienes, stabilization of cell membranes, and/or promotion of the synthesis of nerves or nerve growth factor.

As used herein the meaning of "NMDA-receptor antagonist" or "NMDA antagonist" encompasses compounds that may block or inhibit the action of the N-methyl d-aspartate (NMDA) receptor. The receptor can be deactivated by inhibitors that can cause the NMDAR (NMDA receptor) to close by binding to allosteric sites, e.g., 1) Competitive antagonists, which bind to and block the binding site of the neurotransmitter glutamate; 2) glycine antagonists, which bind to and block the glycine site; 3) noncompetitive antagonists, which inhibit NMDARs by binding to allosteric sites; and 4) uncompetitive antagonists, which block the ion channel by binding to a site within it; or that block the NMDA receptor by another mechanism.

Examples of NMDA-receptor antagonists include, but are not limited to:

Amantadine—"Effects of N-Methyl-D-Aspartate (NMDA)-Receptor Antagonism on Hyperalgesia, Opioid Use, and Pain After Radical Prostatectomy", University Health Network, Toronto, September 2005

Dextromethorphan—Wong B Y, Coulter D A, Choi D W, Prince D A (1988). "Dextrorphan and dextromethorphan, common antitussives, are antiepileptic and antagonize N-methyl-D-aspartate in brain slices". Neurosci. Lett. 85 (2): 261-6.

Dextrorphan—Wong B Y, Coulter D A, Choi D W, Prince D A (1988). "Dextrorphan and dextromethorphan, common antitussives, are antiepileptic and antagonize N-methyl-D-aspartate in brain slices". Neurosci. Lett. 85 (2): 261-6.

Ibogaine—Popik P, Layer R T, Skolnick P (1994): "The putative anti-addictive drug ibogaine is a competitive inhibitor of [3H]MK-801 binding to the NMDA receptor complex." Psychopharmacology (Berl), 114(4), 672-4.

Ketamine—Harrison N, Simmonds M (1985). "Quantitative studies on some antagonists of N-methyl D-aspartate in slices of rat cerebral cortex". Br J Pharmacol 84 (2): 381-91.

Nitrous oxide—Grasshoff C, Drexler B, Rudolph U, Antkowiak B (2006). "Anaesthetic drugs: linking molecular actions to clinical effects". Curr. Pharm. Des. 12 (28): 3665-79; Kolesnikov et al. (1994) Life Sci. 55:1393. Administering inhibitors of nitric oxide synthase in morphine-tolerant animals reverses tolerance, despite continued opioid administration. Kolesnikov et al. (1993) Proc. Natl. Acad. Sci. USA 90:5162.

Phencyclidine (PCP)—

Riluzole—Hugon J (1996). "ALS therapy: targets for the future". Neurology 47 (6 Suppl 4): S251-4.

Tiletamine—Ko J C, Smith T A, Kuo W C, Nicklin C F (1998). "Comparison of anesthetic and cardiorespiratory effects of diazepam-butorphanol-ketamine, acepromazine-butorphanol-ketamine, and xylazine-butorphanol-ketamine in ferrets". Journal of the American Animal Hospital Association 34 (5): 407-16.

Memantine (Axura, Akatinol, Namenda, Ebixa, 1-amino-3,5-dimethylada-mantane)—Chawla, P S; Kochar M S (2006). "What's new in clinical pharmacology and therapeutics". WMJ 105 (3): 24-29.

Dizocilpine (MK-801)—Fix A S, Horn J W, Wightman K A, et al (1993). "Neuronal vacuolization and necrosis induced by the noncompetitive N-methyl-D-aspartate (NMDA) antagonist MK(+)801 (dizocilpine maleate): a light and electron microscopic evaluation of the rat retrosplenial cortex". Exp. Neurol. 123 (2): 204-15.

Aptiganel (Cerestat, CNS-1102)—binds the $Mg^{2+}$ binding site within the channel of the NMDA receptor.

Remacimide—Muir, K W (2005). "Glutamate-based therapeutic approaches: clinical trials with NMDA antagonists". Current Opinion in Pharmacology 6 (1): 53-60.

7-chlorokynurenate—Hartley D M, Monyer H, Colamarino S A, Choi D W (1990). "7-Chlorokynurenate Blocks NMDA Receptor-Mediated Neurotoxicity in Murine Cortical Culture". Eur J Neurosci 2 (4): 291-295.

DCKA (5,7-dichlorokynurenic acid)—Frankiewicz T, Pilc A, Parsons C (2000). "Differential effects of NMDA-receptor antagonists on long-term potentiation and hypoxic/hypoglycaemic excitotoxicity in hippocampal slices". Neuropharmacology 39 (4): 631-42.

Kynurenic acid—Khan M J, Seidman M D, Quirk W S, Shivapuja B G (2000). "Effects of kynurenic acid as a glutamate receptor antagonist in the guinea pig". European archives of oto-rhino-laryngology: official journal of the European Federation of Oto-Rhino-Laryngological Societies (EUFOS): affiliated with the German Society for Oto-Rhino-Laryngology—Head and Neck Surgery 257 (4): 177-81.

1-Aminocyclopropanecarboxylic acid (ACPC)

AP7 (2-amino-7-phosphonoheptanoic acid)—van den Bos R, Charria Ortiz G, Cools A (1992). "Injections of the NMDA-antagonist D-2-amino-7-phosphonoheptanoic acid (AP-7) into the nucleus accumbens of rats enhance switching between cue-directed behaviours in a swimming test procedure". Behav Brain Res 48 (2): 165-70.

APV (R-2-amino-5-phosphonopentanoate)—Abizaid A, Liu Z, Andrews Z, Shanabrough M, Borok E, Elsworth J, Roth R, Sleeman M, Picciotto M, Tschöp M, Gao X, Horvath T (2006). "Ghrelin modulates the activity and synaptic input organization of midbrain dopamine neurons while promoting appetite". J Clin Invest 116 (12): 3229-39.

CPPene (3-[(R)-2-carboxypiperazin-4-yl]-prop-2-enyl-1-phosphonic acid)—Eblen F, Löschmann P, Wüllner U, Turski L, Klockgether T (1996). "Effects of 7-nitroindazole, NG-nitro-L-arginine, and D-CPPene on harmaline-induced postural tremor, N-methyl-D-aspartate-induced seizures, and lisuride-induced rotations in rats with nigral 6-hydroxydopamine lesions". Eur J Pharmacol 299 (1-3): 9-16.

Other NMDA-receptor antagonists include, but are not limited to, eliprodil; iamotrigine; flupirtine; celfotel; levemopamil; pyroloquinoline quinone; cis-4-(phosphonomethyl)-

2-piperidine carboxylic acid; 1-(4-hydroxy-phenyl)-2-(4-phenylsulfanyl-piperidin-1-yl)-propan-1-one; 2-[4-(4-fluoro-benzoyl)-piperidin-1-yl]-1-naphthalen-2-yl-ethanone (E 2001); 3-(1,1-dimethyl-heptyl)-9-hydroxymethyl-6,6-dimethyl-6a,7,8,10a-tetrahydro-6H-benzo[c]chromen-1-ol (HU-211); 1-{4-[1-(4-chloro-phenyl)-1-methyl-ethyl]-2-methoxy-phenyl}-1H-[1,2,4]triazole-3-carboxylic acid amide (CGP 31358); acetic acid 10-hydroxy-7,9,7',9'-tetramethoxy-3,3'-dimethyl-3,4,3,4'-tetrahydro-1H,1'H-[5,5']bi[benzo[g]isochromenyl]-4-yl ester (ES 242-1); 14-hydroxy-11-isopropyl-10-methyl-5-octyl-10,13-diaza-tricyclo[6.6.1.04,15]pentadeca-1,4,6,8(15)-tetraen-12-one; and 4,5-dioxo-4,5-dihydro-1H-benzo[g]indole-2,7,9-tricarboxylic acid (PQQ), 3-((−)-2carboxypiperazin-4-ylpropyl-1-phosphate (CPP); 1-(cis-2-carboxypiperidine-4-yl)methyl-1-phosphonic acid (CGS 19755), D-2-Amino-5-phosphonopentanoic acid (AP5); 2-amino-phosphonoheptanoate (AP7); D,L-(E)-2-amino-4-methyl-5-phosphono-3-pentenoic acid carboxyethyl ester (CGP39551); 2-amino-4-methyl-5-phosphono-pent-3-enoic acid (CGP 40116); (4-phosphono-but-2-enylamino)-acetic acid (PD 132477); 2-amino-4-oxo-5-phosphono-pentanoic acid (MDL 100,453); 3-((phosphonylmethyl)-sulfinyl)-D,L-alanine; amino-(4phosphonomethyl-phenyl)-acetic acid (PD 129635); 2-amino-3-(5-chloro-1phosphonomethyl-1H-benzoimidazol-2-yl)-propionic acid; 2-amino-3-(3-phosphonomethyl-quinoxalin-2-yl)-propionic acid; 2-amino-3-(5-phosphonomethyl-biphenyl-3-yl)-propionic acid (SDZ EAB 515); 2-amino-3-[2-(2-phosphono-ethyl)-cyclohexyl]-propionic acid (NPC 17742); 4-(3-phosphono-propyl)-piperazine-2-carboxylic acid (D-CPP); 4-(3-phosphono-allyl)-piperazine-2-carboxylic acid (D-CPP-ene); 4-phosphonomethyl-piperidine-2-carboxylic acid (CGS 19755); 3-(2-phosphono-acetyl)-piperidine-2-carboxylic acid (MDL 100,925); 5-phosphono-1,2,3,4-tetrahydro-isoquinoline-3-carboxylic acid (SC 48981); 5-(2-phosphono-ethyl)-1,2,3,4-tetrahydro-isoquinoline-3-carboxylic acid (PD 145950); 6phosphonomethyl-decahydro-isoquinoline-3-carboxylic acid (LY 274614); 4-(1H-tetrazol-5ylmethyl)-piperidine-2-carboxylic acid (LY 233053 and 235723); 6-(1H-Tetrazol-5ylmethyl)-decahydro-isoquinoline-3-carboxylic acid (LY 233536); phencyclidine; thienylcyclohexylpiperidine (TCP); N-allyl-normetazocine (SKF 10,047); cyclazocine; (1,2,3,4,9,9a-hexahydro-fluoren-4a-yl)-methyl-amine (PD 137889); (1,3,4,9,10,10a-hexahydro-2H-phenanthren-4-a-yl)-methyl-amine (PD 138289); PD 138558; and quinoxalinediones, such as 6-cyano-7-nitroquinoxaline-2,3-dione (CNQX); 6,7-dinitroquinoxaline-2,3-dione (DNQX); spermine; spermidine; putrescine; arcaine; PEAQX; PPDA; hodgkinsine; dexoxadrol; endopsychosin; etoxadrol; eticyclidine; rhynchophylline; rolicyclidine; tenocyclidine; xenon; 7-chlorokynurenate; CGP-39653; DCKA; kynureneic acid; L-689, 560; CP-101,606; ifenprodil; Ro25-6981; and the like. References that disclose other NMDA-receptor antagonists as well as assays for identifying NMDA-receptor antagonists include Jia-He Li, et al., 38 J. Med. Chem. 1955 (1995); Bigge 45 Biochem. Pharmacol. 1547 (1993); Steinberg et al, 133 Neurosci. Lett. 225 (1991); Meldrum et al., 11 Trends Pharmacol. Sci., 379 (1990); Willetts et al., 11 Trends Pharmacol. Sci. 423 (1990); Faden et al., 13 Trends Pharmacol. Sci. 29 (1992); Rogawski 14 Trends Pharmacol. Sci. 325 (1993); Albers et al, 15 Clinical Neuropharm. 509 (1992); Wolfe et al., 13 Am. J. Emerg. Med., 174 (1995); and Bigge, 45 Biochem. Pharmacol. 1547 (1993); U.S. Pat. No. 6,251,948 (issued Jun. 26, 2001); U.S. Pat. No. 5,985,586 (issued Nov. 16, 1999), and U.S. Pat. No. 6,025,369 (issued Feb. 15, 2000); Jacobson et al., 110 J. Pharmacol. Exp. Ther. 243 (1987); and Thurkauf et al., 31 J. Med. Chem. 2257 (1988), PCT App. No. WO/2004/045601, all of which citations are hereby expressly incorporated herein by reference.

The NMDA antagonist may be an NMDA antagonist that would not be considered for general clinical use by itself, particularly in higher amounts or usage, due to its side effects. In some embodiments, the NMDA antagonist is a non-competitive channel blocker such as PCP, nitrous oxide, ketamine, MK-801, dextromethorphan, amantadine, dextromethorphan, ibogaine, ketamine, norketamine, memantin, riluzole, tiletamine, dextrorphan, and phencyclidine, and the like. Other compounds with NMDA receptor antagonist activities that are existing pharmaceuticals or nutraceuticals (e.g., have undergone one or more regulatory trials in humans or animals (e.g., FDA based Phase I, Phase II and/or Phase III trials) are also within the scope of the invention. In one embodiment, the NMDA-receptor antagonist described herein is a non-competitive NMDA-receptor antagonist, more preferably, ketamine or norketamine, even more preferably, ketamine hydrochloride.

Ketamine is an N-methyl-D-aspartate (NMDA) calcium channel antagonist that can be admixed in the compositions described herein in concentrations ranging from 10-50%, preferably 10 to 40%, and most preferably from 15% to 20% or to 25%-30%. In some embodiments, the topical formulation has about 15% ketamine. In some embodiments, the topical formulation has about 20% ketamine. In some embodiments, the topical formulation has about 25% ketamine.

In general, the amount of NMDA-receptor antagonist in the compositions of the invention is within the range of from about 0.1 percent to about 100 percent of the total weight of the composition, more preferably, of from about 3 percent to about 50 percent of the total weight of the composition. More preferably, the range is from about 10 percent to about 40 percent of the total weight, and includes the ranges, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40. For example, the amount of ketamine in the invention composition is within the range of from about 5% to about 40%, more preferably from about 10% to about 40, more preferably from about 15% to about 30%, even more preferably from about 20% to about 25%, or alternatively, greater than 10% or 15%. Such ranges of NMDA antagonist employed in the present invention would likely, prior to applicant's disclosure, be considered too high for clinical application, e.g., too high for one time use or, alternatively, too high for repeated use particularly on a large population of patients.

Without being bound to any particular theory of mechanism, the compositions described herein provide an effective antineuropathic response through two compounds that in combination provide effective analgesia with a low or reduced side effect profile. For example, the formulations in combination would provide a lower side effect profile than the individual components taken independently, particularly in higher concentrations or dosages. Other properties which may be considered is the effective half life of the composition, the ability to cross or not cross the blood brain barrier, the ability of the compound to remain local in proximity to the topical administration, increase or decrease in blood pressure, psychomimetic symptoms, drowsiness, and the like. Those of skill in the art will recognize compounds and side effect profiles of compounds suitable in the present invention.

As used herein, the phrase "side effects" encompasses unwanted and adverse effects of a therapy (e.g., a prophylactic or therapeutic agent). An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, psychotomimetic effects, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra pyramidal symptoms, akathisia, cardiovascular disturbances and sexual dysfunction.

Many drugs have been found that lessen the risk of neurotoxicity from NMDA receptor antagonists that can used as the second active compound within the formulations described herein in order to reduce unwanted side effects. Centrally-acting alpha-2 agonists such as clonidine and guanfacine are thought to most specifically target the etiology of NMDA neurotoxicity (see, e.g., US Pat. App. Nos. 20050148673, 20050222270, 20020068754 and 20020016319, and PCT App. No. WO/2001/089448A2). Other drugs acting on various neurotransmitter systems known to inhibit NMDA antagonist neurotoxicity include: anticonvulsants or antiepileptics, anticholinergics (see, e.g., U.S. Pat. Nos. 5,034,400, 5,616,580, 5,605,911, 5,767,130 and 5902815), tri-cyclo-alkyl-amine (TCAA) structure (US Pat. No. 20020177592) diazepam, barbiturates [Olney J, Labruyere J, Wang G, Wozniak D, Price M, Sesma M (1991). "NMDA antagonist neurotoxicity: mechanism and prevention". Science 254 (5037): 1515-8; U.S. Pat. No. 5,474,990], ethanol [Farber N B, Heinkel C, Dribben W H, Nemmers B, Jiang X. (2004). "In the adult CNS, ethanol prevents rather than produces NMDA antagonist-induced neurotoxicity". Brain Res 1028(1):66-74], 5-HT2A serotonin agonists [Farber N, Hanslick J, Kirby C, McWilliams L, Olney J (1998). "Serotonergic agents that activate 5HT2A receptors prevent NMDA antagonist neurotoxicity". Neuropsychopharmacology 18 (1): 57-62.], risperidone and muscimol [Maas, Al (2001). "Neuroprotective agents in traumatic brain injury". Expert Opin Investig Drugs. 10(4):753-67; Tryba M, Gehling M. Clonidine—a potent analgesic adjuvant. Curr Opin Anaesthesiol. 2002 October; 15(5):511-7].

The anticonvulsants, also called antiepileptic drugs (abbreviated "AEDs"), belong to a diverse group of pharmaceuticals used in prevention of the occurrence of epileptic seizures. Anticonvulsants are also increasingly finding ways into the treatment of bipolar disorder, since many seem to act as mood stabilizers. The goal of an anticonvulsant is to suppress the rapid and excessive firing of neurons that start a seizure. Failing this, a good anticonvulsant would prevent the spread of the seizure within the brain and offer protection against possible excitotoxic effects that may result in brain damage. Certain anticonvulsants prevents Olney vacuole formation neurotoxicity of MK-801, an NMDA antagonist, when injected into female rats, see Farber, N B, et al. "Antiepileptic drugs and agents that inhibit voltage-gated sodium channels prevent NMDA antagonist neurotoxicity." Mol Psychiatry 2002; 7(7): 726-733.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clobazam, clonazepam, decimemide, diethadione, dimethadione, doxenitroin, eterobarb, ethadione, ethosuximide, ethotoin, felbamate, fluoresone, fosphenyloin, gabapentin, 5-hydroxytryptophan, lamotrigine, levetiracetam, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabalin, primidone, progabide, sodium bromide, sodium valproate, solanum, strontium bromide, suclofenide, sulthiame, tetrantoin, tiagabine, topiramate, trimethadione, valproate semisodium, valproic acid, valpromide, vigabatrin, and zonisamide, and derivatives thereof.

Gabapentin is a glutamate antagonist at the NMDA and AMPA (sodium channel) receptor sites. This agent can be admixed in strengths ranging from 1 to 30 percent, preferably strengths less than 15%, more preferably in strengths 10% or less, including in 1, 2, 3, 4, 5, 6, 7 and 8%. In one embodiment, the formulation has 3%-6% gabapentin, but it can be included in amounts of 1%, 2%, 4%, 5%, 7%, 8%, 9%, or therebetween. More dosing flexibility is allowed transdermally because of its relatively low systemic concentration. See Bakonja M, Baydoun A, Edwards K R, et al. "Gabapentin for the symptomatic treatment of painful neuropathy in patients with diabetes mellitus—a randomized controlled trial." JAMA 1998; 280: 1831-1836. Also see Rowbatham M, Hardin N, Stacey B, et al. "Gabapentin for the treatment of postherpetic neuralgia—a randomized controlled trial." JAMA 1998; 280: 1837-1842.

In an alternative embodiment of the compositions described herein, other active components can be used to potentiate the action of NMDA-receptor antagonists such as ketamine. For example, analgesics can be any known in the art, including, but not limited to NMDA ligands, AMPA ligands, non-NMDA or AMPA ligands, TNF-1α ligand, GABA ligand, α-2 ligands, and the like. Such analgesics can include clonidine, capsaicin, lidocaine, bupivacaine, mepivacaine, ropivacaine, tetracaine, etidocaine, chloroprocaine, prilocalne, procaine, benzocaine, dibucaine, dyclonine hydrochloride, pramoxine hydrochloride, benzocaine, lacosamide and proparacaine. It is preferable that the topical formulation have as little of a side effect profile for a large population of patients.

In addition, the compositions described herein can further comprise additional ingredients that can increase the analgesic effectiveness of the combination of invention composition. Such ingredients can facilitate the effect of this combination or compounds by increasing absorption and/or penetration, provide for a more comprehensive pain management regimen, decrease the side effect profile of the base composition, or the like. For example, magnesium ions (e.g., from magnesium oxide or other magnesium preparations) antagonize ionic calcium in the nervous system, enhancing the effect of the present invention. Those of skill in the art will readily recognize additional ingredients that can be admixed in the compositions described herein.

In some compositions, co-administration with a magnesium salt may increase the pain-relieving efficacy of this treatment in at least some cases. As used herein, the term "salt" includes any compound or complex that releases substantial quantities of free magnesium ions (Mg++) when dissolved in an aqueous solution.

Nerve impulse conduction is blocked by a decrease in nerve cell membrane permeability to sodium ions, possibly by competing with calcium-binding sites that control sodium permeability. This change in permeability results in decreased depolarization and an increased excitability threshold that ultimately prevents the nerve action potential from forming.

Ionic calcium is antagonized by magnesium ions in the nervous system. Because of this, dietary supplements of magnesium oxide and other magnesium preparations may increase or enhance the effects of calcium channel blockade.

Magnesium can effect muscle relaxation through direct action on the cell membrane. Mg++ ions close certain types of calcium channels, which conduct a positively charged calcium ion into the neuron. With an excess of magnesium, more channels will be blocked and the nerve will have less activity.

The compositions described herein can further comprise non-physiologically active ingredients or components usually admixed in such topical preparations (besides an NMDA antagonist and a second active ingredient, such as an anticonvulsant). For example, the compositions may also include additional ingredients such as other carriers, moisturizers, oils, fats, waxes, surfactants, thickening agents, antioxidants, viscosity stabilizers, chelating agents, buffers, preservatives, perfumes, dyestuffs, lower alkanols, humectants, emollients, dispersants, sunscreens such as radiation blocking compounds or particularly UV-blockers, antibacterials, antifungals, disinfectants, vitamins, antibiotics, or other anti-acne agents, as well as other suitable materials that do not have a significant adverse effect on the activity of the topical composition. Additional inactive ingredients for inclusion in the carrier may be sodium acid phosphate moisturizer, witch hazel extract carrier, glycerin humectant, apricot kernel oil emollient, corn oil dispersant, and the like which are further detailed below. Those of skill in the art will readily recognize additional inactive ingredients, which can be admixed in the compositions described herein.

In addition to the foregoing components, the compositions described herein can optionally contain other ingredients. For example, triethanolamine can be added as a crosslinking agent. A preservative, such as betahydroxytoluene can also be added. Other irritation reducing agents can be added too. In this regard, irritation reducing agents can include, but are not limited to, glycerol. In some instances, semi-solid testosterone formulations have been prepared with propylene glycol and/or butylene glycol as the glycol component, ethyl alcohol and/or isopropyl alcohol as the alcohol component. Preservatives, a cross-linking agent, and additional irritation reducing agents can be included in formulations prepared in accordance with the methods described.

The compositions and methods of the invention are effective to induce local anaelgesia and to treat neuropathic pain. As used herein the term "neuropathic pain" refers to neuropathic-pain syndromes, that is, pain due to lesions or dysfunction in the nervous system. The compositions and methods of the invention can be used to treat or prevent pain related to or induced by the following diseases, trauma, or conditions: general neuropathic conditions, such as peripheral neuropathy, phantom limb pain, reflex-sympathetic dystrophy, causalgia, syringomyelia, and painful scar; specific neuralgias at any location of the body; back pain; diabetic neuropathy; alcoholic neuropathy; metabolic neuropathy; inflammatory neuropathy; chemotherapy-induced neuropathy, herpetic neuralgias; traumatic odontalgia; endodontic odontalgia; thoracic-outlet syndrome; cervical, thoracic, or lumbar radiculopathies with nerve compression; cancer with nerve invasion; traumatic-avulsion injuries; mastectomy, thoracotomy pain; spinal-cord-injury; stroke; abdominal-cutaneous nerve entrapments; tumors of neural tissues; arachnoiditis; stump pain; fibromyalgia; regional sprains or strains; myofascial pain; psoriatic arthropathy; polyarteritis nodosa; osteomyelitis; burns involving nerve damage; AIDS-related pain syndromes; connective tissue disorders, such as systemic lupus erythematosis, systemic sclerosis, polymyositis, and dermatomyositis; and inflammatory conditions, such as acute inflammation (e.g. trauma, surgery and infection) or chronic inflammation (e.g., arthritis and gout).

The term "active", "active compound" or "active ingredient" means a compound or ingredient that exerts a physiological affect. For example, compounds that reduce, eliminate, or alleviate the side effects of an NMDA-receptor antagonist would be active compounds. Inactive compounds or ingredients are those that do not exert a physiological effect on a patient or subject or do not reduce, eliminate, or alleviate side effects of NMDA-receptor antagonists.

Topical application of the composition may be useful for relieving pain, inflammation and irritation associated with skin diseases and disorders, such as psoriasis, pruritus, and lesions. Painful lesions develop, for example, from viral infections, skin cancers and genetic disorders. Topical application of the composition provides relief from pain associated with wounds, insect and animal bites, abrasions and burns, including those resulting from over-exposure to the sun, chemicals, radiation or chemotherapeutic agents. Acute postoperative or surgical pain can be reduced or even prevented, as can pain associated with chronic disorders, such as arthritis.

In some embodiments the methods described herein can provide a treatment of applying the compositions described herein to an affected area of a subject with diabetic polyneuropathy. In other aspects, the methods described herein can include treating peripheral neuropathy, comprising the step of topical administration of a pharmaceutical composition of ketamine in a topical vehicle to the affected area of a subject in need of such treatment.

Thus, the methods and compositions described herein can be effective for neuropathies, particularly peripheral neuropathies, associated with diseases such as: uremia; childhood cholestatic liver disease; chronic respiratory insufficiency; alcoholic polyneuropathy; multiple organ failure; sepsis; hypoalbuminemia; eosinophilia-myalgia syndrome; hepatitis; porphyria; hypoglycemia; vitamin or nutritional deficiency (e.g., B-12 deficiency); chronic liver disease; primary biliary cirrhosis; hyperlipidemia; leprosy; Lyme disease; herpes zoster; Guillain-Barre syndrome; chronic inflammatory demyelinating polyradiculoneuropathy; sensory perineuritis; HIV or acquired immunodeficiency syndrome (AIDS)—associated neuropathy; Sjogren's syndrome; primary vasculitis (such as polyarteritis nodosa); allergic granulomatous angiitis; hypersensitivity angiitis; Wegener's granulomatosis; Raynaud's Phenomenon, including CREST syndrome, autoimmune diseases such as erythromatosis (systemic lupus erythematosis); rheumatoid arthritis or other rheumatoid diseases; mixed connective tissue disease; scleroderma; sarcoidosis; vasculitis; systemic vasculitides; acute tunnel syndrome; pandysautonomia; primary, secondary, localized or familial systemic amyloidosis; hypothyroidism; chronic obstructive pulmonary disease; acromegaly; malabsorption (sprue, celiac disease); carcinomas (sensory, sensorimotor, late and demyelinating); lymphoma (including Hodgkin's), polycythemia vera; multiple myeloma (lytic type, osteosclerotic, or solitary plasmacytoma); benign monoclonal gammopathy; macroglobulinemia; cryoglobulinemia; tropical myeloneuropathies; herpes simplex infection; cytomegalovirus infection; cranial nerve palsies; drug-induced neuropathy; industrial neuropathy; lymphomatous neuropathy; myelomatous neuropathy; multi-focal motor neuropathy; immune-mediated disorders, chronic idiopathic sensory neuropathy; carcinomatous neuropathy; acute pain autonomic neuropathy; alcoholic neuropathy; compressive neuropathy; vasculitic/ischaemic neuropathy; mono- and polyneuropathies; and diabetes.

Genetically acquired neuropathies suitable for treatment by the methods and compositions described herein include, without limitation: peroneal muscular atrophy (Charcot-Marie-Tooth Disease) hereditary amyloid neuropathies, hereditary sensory neuropathy (type I and type II), porphyric neuropathy, hereditary liability to pressure palsy, Fabry's Disease, adrenomyeloneuropathy, Riley-Day Syndrome, Dejerine-Sottas neuropathy (hereditary motor-sensory neuropathy-III), Refsum's disease, ataxia-telangiectasia, hereditary tyrosinemia, anaphalipoproteinemia, abetalipoproteinemia, giant axonal neuropathy, metachromatic leukodystrophy, globoid cell leukodystrophy, and Friedrich's ataxia.

In alternative embodiments compositions described herein are directed to treatment of neuropathic pain, especially pain caused by nerve injury or sympathetically mediated pain. Sympathetically mediated pain (SMP) is a type of pain in which over activity of the sympathetic nervous system plays a crucial role. It includes the syndromes of reflex sympathetic dystrophy (RSD), causalgia, neuropathic pain secondary to nerve injury, and pain from neuromas. It encompasses all neurogenic pain that is not central and is related to a nerve injury regardless of the cause. Neuropathic pain syndromes include, without limitation (other than the neuropathies described herein), allodynia, various neuralgias such as post herpetic neuralgia and trigeminal neuralgia, phantom limb pain, hyperpathia, hyperesthesia, hyperalgesia, dyesthesia, paresthesia, anesthesia delorosa, deafferatation pain, and complex regional pain syndromes (CRPS), such as reflex sympathetic dystrophy (RSD) and causalgia. Specific examples include low back pain, sciatica, Guillain-Barre Syndrome, post-surgical traumatic neuropathy, and diabetic peripheral polyneuropathy.

Formulations

The formulations in which the compositions described herein are incorporated can assume any of a variety of dosage forms, including solutions, suspensions, ointments, and solid inserts. Examples are creams, lotions, gels, ointments, suppositories, sprays, foams, liniments, aerosols, buccal and sublingual tablets, various passive and active topical devices for absorption through the skin and mucous membranes, including transdermal applications, and the like.

Typical pharmaceutically acceptable carriers are, for example, water, mixtures of water and water-miscible solvents such as lower alkanols or vegetable oils, and water-soluble ophthalmologically acceptable non-toxic polymers, for example, cellulose derivatives such as methylcellulose. A typical cream or ointment-type carrier for topical application that can be used according to the methods and compositions described herein include a mixture of water, glycerin, propylene glycol, and methylparaben. Topical carriers may also include other conventional emulsifiers and emollients including alginates, glyceryl stearate, PEG-100 stearate, cetyl alcohol, propylparaben, butylparaben, sorbitols, polyethoxylated anhydrosorbitol monostearate (TWEEN), white petrolatum (VASELINE), triethanolamine, Emu oil, aloe vera extract, lanolin, cocoa butter, and the like. Suitable topical carriers are well known to the skilled artisan.

Preferably, Lipoderm® (Professional Compounding Centers of America, Houston, Tex.) is admixed in the compositions described herein. Alternative ointment bases are known to persons skilled in the art such as Transcutol-P (ethoxydiglycol, commercially available, for example, from Gattefosse, Westwood, N.J.). Sufficient Lipoderm® base is admixed to act as a carrier for the active ingredients of the composition. Typically the Lipoderm® base will make up more than about 50% of the total composition and more preferably about 70% of the composition is the Lipoderm® base. The Lipoderm® base functions as a carrier and enhances penetration through the skin. It is also hypoallergenic and is aesthetically pleasing.

The terms "matrix," "matrix system," or "matrix patch" relate to an active permeant or drug dissolved or suspended in a biocompatible polymeric phase, preferably a pressure sensitive adhesive, that can also contain other ingredients or in which the enhancer is also dissolved or suspended. This definition is meant to include embodiments wherein such polymeric phase is laminated to a pressure sensitive adhesive or used with an overlay adhesive. A matrix system usually and preferably comprises an adhesive layer having an impermeable film backing laminated onto the distal surface thereof and, before transdermal application, a release liner on the proximal surface of the adhesive. The film backing protects the polymeric phase of the matrix patch and prevents release of the drug and/or enhancer to the environment. The release liner functions similarly to the impermeable backing, but is removed from the matrix patch prior to application of the patch to an application situs. Matrix patches are known in the art of transdermal drug delivery to routinely contain such backing and release liner components, and matrix patches according to the compositions described herein should be considered to comprise such backing and release liner or their functional equivalents. U.S. Pat. No. 5,122,383 (incorporated herein by reference) describes such backing and release liner. A matrix system therefore relates to a unit dosage form of a drug composition in a polymeric carrier, also containing the enhancer and other components that are formulated for maintaining the drug composition in the polymeric layer in a drug transferring relationship with the derma, i.e. the skin or mucosa. A matrix patch is distinguished from a "liquid reservoir patch," wherein an active permeant or drug is dissolved in a gelled liquid contained in an occlusive device having an impermeable back surface and an opposite surface configured appropriately with a permeable membrane and adhesive for transdermal application, e.g., U.S. Pat. No. 4,983,395, incorporated herein by reference in its entirety.

A typical transdermal formulation comprises a conventional aqueous or non-aqueous vehicle, for example, a cream, ointment lotion or paste or in the form of a medicated plaster, patch or membrane.

The term "effective amount" of a drug or permeant relates to a nontoxic but sufficient amount of a compound to provide the desired local or systemic effect without adverse side effects. An "effective amount" of permeation enhancer as used herein relates to an amount selected so as to provide the desired increase in membrane permeability and, correspondingly, the desired depth of penetration, rate of administration, and amount of drug.

As used herein, "application situs" relates to a site suitable for topical application with or without the means of a device, patch, or dressing, e.g. the spinal column, behind the ear, on the arm, back, chest, abdomen, leg, top of foot, etc. For example, the cream can be applied to the site of pain or the spine dermatome(s) of the pain site, e.g., L2-S2 for any leg, knee, or foot neuropathy.

As used herein, transdermal delivery also includes numerous different systems for the transdermal delivery of active agents known in the art. Transdermal delivery systems include but are not limited to passive devices such as drug-in-adhesive transdermal patches and "active" transdermal technologies such as iontophoresis, electroporation, sonophoresis, magnetophoresis, microneedle devices and those devices that use thermal energy to make the skin more permeable.

Transdermal drug delivery devices are available from the 3M Drug Delivery Systems Division (St. Paul, Minn., USA), Noven Pharmaceuticals, Inc. (Miami, Fla., USA), ImaRx (Tucson, Ariz., USA), Elan Corporation (Dublin, Ireland), Novosis AG (Miesbach, Germany), Ultrasonic Technologies (St. Albans, Vt., USA), Antares Pharma (Exton, Pa., USA), Altea Therapeutics (Tucker, Ga., USA), Iomed, Inc. (Salt Lake City, Utah, USA), MacroChem Corp (Lexington, Mass., USA), Sontra Medical Corporation (Franklin, Mass., USA), Vyteris, Inc. (Fair Lawn, N.J., USA), BioChemics, Inc. (Danvers, Mass., USA), A.P Pharma (Redwood, City, Calif., USA), MIKA Pharma GmbH (Limburgerhof, Germany), NexMed, Inc. (Robbinsville, N.J., USA), Encapsulation Systems, Inc. (Springfield, Pa., USA), Acrux Ltd (Elgin, Ill., USA), Jenapharm GmbH (Berlin, Germany), Norwood Abbey (Victoria, Australia), Novavax (Columbia, Md., USA), Genetronics Biomedical Corporation (San Diego, Calif., USA), Adherex Technologies (Research Triangle Park, N.C., USA), and AlphaRx (Ontario, Canada).

Penetration Enhancers

In another embodiment, the compositions of the invention can further comprise inactive compounds, such as penetration enhancers. When present in a composition of the invention, the amount of penetration enhancer is preferably from about 1% to about 10% by weight of the total composition weight, more preferably from about 2% to about 5% by weight.

Penetration enhancers can be included in some embodiments to optimize transfer of the NMDA-receptor antagonist through the stratum corneum and into the dermis/dermatome to provide a local effect. For a discussion of use of penetration enhancers in topical formulations see generally, Percutaneous Penetration Enhancers (Eric W. Smith & Howard I. Maibach eds. 1995); Ghosh, T. K. et al. 17 Pharm. Tech. 72 (1993); Ghosh, T. K. et al. 17 Pharm. Tech. 62 (1993); Ghosh, T. K. et al. 17 Pharm. Tech. 68 (1993), all of which citations are hereby incorporated herein by reference. The penetration enhancer should be pharmacologically inert, non-toxic, and non-allergenic, have rapid and reversible onset of action, and be compatible with the compositions of the invention.

Examples of penetration enhancers include, but are not limited to, transcutol P, ethyl alcohol, isopropyl alcohol, lauryl alcohol, salicylic acid, octolyphenylpolyethylene glycol, polyethylene glycol 400, propylene glycol, N-decylmethylsulfoxide, DMSO and the azacyclo compounds, as disclosed in U.S. Pat. Nos. 4,755,535; 4,801,586; 4,808,414; and 4,920,101, all of which patents are hereby expressly incorporated herein by reference. Preferably, the penetration enhancer is transcutol P.

Methods of Manufacture

The compositions of the invention are prepared according to standard methods, well known in the art, for preparing emulsions for topical administration. For example, the methods recited in Gennaro, A. R., Remington: The Science and Practice of Pharmacy, 21st edition, Lippincott, Williams & Wilkins (2006), hereby expressly incorporated herein by reference, can be used. Also, Example preparations are recited in the Example section below.

The compositions described herein can be made by cold compounding. This is significant since one or more of the compounds admixed in the topical compositions described herein may be sensitive to heat or other types of energy. Thus the activity of the composition may be detrimentally affected as a result of the formulation of the compositions in other manners. Preferably, the ingredients of this topical composition can be merely mixed together, without heating and using a sufficient amount of the carrier to provide a substantially homogeneous cream or gel. It is generally preferred to dissolve, disperse or suspend one or more of the ingredients prior to cold compounding in order to ensure substantially homogeneous distribution of the active ingredients in the composition.

Alternatively, the components can be separated into those that are water-soluble and those that are oil-soluble. The water-soluble components can be mixed together in one vessel to form a solution and the oil-soluble components can be mixed together in a separate vessel and heated (e.g., 70° C. to 80° C.) to form a solution. The two solutions can then be mixed and the mixture allowed to cool. This method requires nothing more than two beakers and a heating apparatus. Homogenation is achieved using a high-shear rate blender or other suitable apparatus. The appropriate droplet size is achieved by standard adjustment of the shear rate during high-speed mixing followed by droplet size analysis as described in Gennaro, A. R., Remington: The Science and Practice of Pharmacy, 21st edition, Lippincott, Williams & Wilkins (2006) and Allen & Terence, Particle Size Measurement 483 (4th ed. 1990, both or which citations are hereby expressly incorporated herein by reference. Suitable equipment and methods for preparing emulsions and compositions of the invention, such as high-shear rate blenders are described in 2 Remington: The Science and Practice of Pharmacy 1509-1515 (Alfonso R. Gennaro ed., 19th ed. 1995) (updated in Gennaro, A. R., Remington: The Science and Practice of Pharmacy, 21st edition, Lippincott, Williams & Wilkins (2006)), hereby expressly incorporated herein by reference. Methods for preparation of emulsions for topical administration, suitable for preparing compositions of the invention, are also described in Bernard Idson, Pharmaceutical Emulsions in 1 Pharmaceutical Dosage Forms: Disperse Systems 199 (Herbert A. Lieberman et al. eds. 1988), hereby expressly incorporated herein by reference.

The compositions are then packaged and stored according to well-known methods. For example, see the packaging procedures described in 1 Remington: The Science and Practice of Pharmacy 390-391 (Alfonso R. Gennaro ed., 19th ed. 1995—updated in Gennaro, A. R., Remington: The Science and Practice of Pharmacy, 21st edition, Lippincott, Williams & Wilkins (2006)), hereby incorporated herein by reference. If desired, the compositions of the invention can be sterilized according to well-known methods, for example, the methods described in 2 Remington: The Science and Practice of Pharmacy 1463-1486 (Alfonso R. Gennaro ed., 19th ed. 1995— updated in Gennaro, A. R., Remington: The Science and Practice of Pharmacy, 21st edition, Lippincott, Williams & Wilkins (2006)), hereby incorporated herein by reference.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 15% to about 30%" should be interpreted to include not only the explicitly recited values of about 15% to about 30%, but also include individual values and subranges within the indicated range. Thus, included in this numerical range are individual values such as 15, 16, 17, 18, 19, 20, 21, 22, 23, 24, 25, 26, 27, 28, 29, and 30, and sub-ranges such as from 15 to 25, 20 to 25, and from 20 to about 30, etc. This same principle applies to ranges reciting only one numerical value. Furthermore, such an interpretation should apply regardless of the breadth of the range or the characteristics being described.

Application

The general mode of action of the composition is through "topical administration." The term "topical administration" or "topical application" refers to directly layering or spreading upon epidermal tissue, especially outer skin or membrane, including but not limited to the skin or membrane of cutaneous, mucosal or oral, vaginal, rectal, ocular, or nasal surfaces or cavities. The composition is topically administered to a subject in an amount and duration sufficient to prevent or relieve pain associated with any cause, including, but not limited to, neuropathic inflammation, and acute and chronic peripheral neuropathy.

Examples of patches suitable for use with compositions of the invention include (1) the matrix-type patch; (2) the reservoir-type patch; (3) the multi-laminate drug-in-adhesive type patch; (4) the monolithic drug-in-adhesive type patch; and (5) hydrogel patch; see generally Ghosh, T. K.; Pfister, W. R.; Yum, S. I. Transdermal and Topical Drug Delivery Systems, Interpharm Press, Inc. p. 249-297, hereby expressly incorporated herein by reference). These patches are well known in the art and available commercially.

In general, the active ingredient (e.g., NMDA antagonist, optionally combined with anticonvulsants or other compounds which may reduce the side effects of NMDA antagonists, analgesics, and the like) of the invention will comprise from about 0.5 percent to about 40 percent by weight of the patch, preferably from about 10 percent to about 30 percent, more preferably from about 15 percent to about 25 percent, and most preferably from about 18 percent to about 22 percent by weight of the patch.

With gels, creams, or ointments, typically 1 to 10 applications are required per day. Generally, about 0.1 g/cm² of skin area to about 5 g/cm², preferably 1 g/cm² to about 2 g/cm² of a composition of the invention is administered to and around the application site.

When a patch is used to administer a composition of the invention, the dosage to achieve pain relief is determined by the active surface area of the medicated portion of the patch in direct contact with the skin. Several dosage strengths are advantageous depending upon the severity of the wound. In general, a physician can begin dosing with a low or intermediate strength patch and then, depending upon the effectiveness, adjust the dosage up or down by prescribing a patch of higher or lower active concentration or a patch of larger or smaller surface area, or, in some cases, multiple patches. In general, the composition of the invention will comprise from about 0.5 percent to about 20 percent by weight of the patch, preferably from about 5 percent to about 25 percent by weight of the patch. For matrix (drug-in-adhesive) type patches, the compositions of the invention will comprise from about 0.5 percent to about 20 percent by weight of the patch. For patches comprising a hydrogel, the compositions of the invention will comprise from about 0.5 percent to about 10 percent by weight of the patch. Fresh patches may be administered multiple times per day, but, preferably, a fresh patch is administered about every 18 to about every 48 hours, more preferably daily.

EXAMPLES

All chemicals used in the following examples are available from commercial sources in the United States of America for instance, Hawkins Pharmaceuticals (Minneapolis, Minn.) or B&B Pharmaceuticals (Aurora, Colo.). The preferred transdermal base "Lipoderm" is only available from the Professional Compounding Centers of America (PCCA). However, other transdermal bases are available from Hawkins Pharmaceuticals (e.g., "Lipo Cream") or from Medisca, Inc. (Plattsburg, N.Y.). "Krisgel" (a thickener) is available only from PCCA, but similar commercial products are available from other chemical suppliers, e.g., "Tommy Gel" from Hawkins Pharmaceuticals. All reagents used in the Examples below are also commercially available from international standard sources, for example from, Spectrum Laboratory Products, Inc. Gardena, Calif.; Lab Express International Inc. NJ; AK Chemical Tech and Shandong Zhonggong Chemical Co. Ltd., Shanghai Gupeng International Trading Co., Ltd., Beijing Medicine Chemical Co., Ltd., in China; Greenspharma, Maps Pharmaceuticals of India. Additional searches online will result in additional sources for such compounds. One source for gabapentin is Spectrum Laboratory Products, Inc. and ketamine hydrochloride is from Medisca, Inc., Plattsburg, N.Y.

Transdermal bases differ from topical bases, e.g., petrolatum or cold cream, in that they facilitate the penetration of the active chemicals through all dermal layers. This subcutaneous entry, in turn, allows the active chemicals to penetrate the nerve fibers themselves. The PCCA transdermal base Lipoderm is preferred due to its proven penetration superiority over PLO (pluronic-lecithin-organogel).

Formulation

Ketamine HCl and Gabapentin powders can be accurately weighed by any FDA-approved scale. Water is measured using any approved cylindrical graduate. The powders are first filtered through a fine-mesh screen into a glass mortar then dissolved by the addition of water. An electronic mortar and pestle (EMP) is equally suitable in place of a manual glass mortar and pestle. The Lipoderm (or similar) transdermal base is then geometrically levigated into the dissolved powders. Krisgel (or similar) is then stirred into the mixture until evenly distributed. The mixture is then milled in a three-roller ointment mill (Exakt 50 or similar) and then dispensed in an appropriate ointment jar. Gabapentin can also be in weights of 3%.

Gabapentin can also be in weights of 3% with an increase in the amount of the Lipoderm Base.

The anticipated dose of Neurocreme is up to 2-5 grams per day. This dose translates to a topical administration of 400 mg of ketamine hydrochloride and 60 mg of gabapentine.

In one example, the active ingredients of the compositions described herein are composed of two chemicals within a transdermal base. The chemicals are (1) ketamine hydrochloride, an N-methyl-D-aspartate (NMDA) calcium channel antagonist in concentrations of 15% or 20% when combined with gabapentin. (2) Gabapentin, a glutamate antagonist at the NMDA and AMPA (sodium channel) receptor sites. Its concentration is typically 3%, but can be increased to 6% or decreased for gabapentin-sensitive patients. The transdermal vehicle Lipoderm® is used. This vehicle is a gel, but has the appearance and feel of a cream. It has the exceptional ability to contain up to 50% of its weight in active drugs. It is also cosmetically elegant and has a hypoallergenic compatibility with human dermis. The combination of the 2 agents within the Lipoderm® base act synergistically to relieve neuropathic pain.

One method of preparation is as follows. Ketamine and gabapentin powders were filtered through a fine-mesh screen into the appropriate vessel (e.g., a glass mortar.) Powders were wetted with sufficient propylene glycol. Some Lipoderm® was added to suspend the wet powders. The remainder of Lipoderm® was added and triturated till mixed. Krisgel®

1% (of the total compound) was added to thicken. An ointment mill was used to completely mix and smooth the cream. The resulting cream looks and feels like custard.

Aqueous-Phase Solution: Sorbitol solution, water, and PEG-100 stearate, were added to a Groen kettle (Model "TDB/8-20 CFC", Groen Division, Dover Corporation, Elk Grove Village, Ill.). The kettle has a self-contained water jacket. The temperature was maintained within the range of about 70° C. to about 80° C. The kettle was covered, and the mixture was heated and stirred. When a solution resulted, the methylparaben, ketamine hydrochloride, and gabapentin were added. Stirring and heating continued until all ingredients were dissolved.

Oil-Phase Solution: Cetyl alcohol, isopropyl myristate, glycerol stearate and petrolatum were added to a stainless-steel container immersed in a hot water bath. The water-bath temperature was maintained in the range of 70° C. to 80° C. using a hot-plate. The solution was heated and stirred (Lab-Stirrer, Model LR 400 C, Fisher Scientific Inc., Pittsburgh, Pa.) until a homogenous liquid resulted. Propylparaben was then added and stirring and heating continued until the propylparaben was completely dissolved.

The oil phase (70° C.) was slowly poured into the aqueous phase (70° C.) and the resulting mixture stirred for 10 minutes using the kettle-stirring device. The kettle stirring device was then disassembled and the mixture emulsified using a high-shear homogenizer (PowerGen Homogenizer, Model 700D, Fisher Scientific Inc., Pittsburgh, Pa.) for 15 minutes. The kettle stirring device was reassembled to stir the resulting emulsion while the hot water in the kettle jacket was replaced with ice water to cool the emulsion. After the emulsion temperature dropped below 40° C., simethicone was added and the emulsion was then mixed for another 15 minutes using the kettle-stirring device. A Grisona MA filling machine (NAG Nahma AG, Unterageri, Austria) was used to fill the emulsion into 60 gram aluminum tubes (Peerless Tube Company, Bloomfield, N.J.).

The oil-phase-droplet diameters (weight mean diameter) were measured via laser-light diffraction (Malvern Mastersizer S Laser Diffractor, Malvern Instruments Ltd, Malvem, UK). Prior to the analysis, emulsion samples were dispersed in a 6.5% solution of PEG-100 stearate in purified water. Sample refractive index and carrier-fluid refractive index were set at 1.5295 and 1.33, respectively. The default setting for the Presentation and Analysis Model is "OHD" and "Polydisperse".

Gabapentin and ketamine hydrochloride were dissolved in the water in a glass beaker. Methylparaben and propylparaben were mixed with Transcutol-P in a separate beaker. The Transcutol-P solution containing the methylparaben and propylparaben was poured into the gabapentin/ketamine hydrochloride solution. A glass beaker containing the above solution was then placed inside a ice bath to cool the solution to approximately 5° C. Pluronic F127 was added to the solution with continuous mixing (Lab-Stirrer, Model LR 400 C, Fisher Scientific Inc., Pittsburgh, Pa.) for approximately 12 hours until a clear solution resulted. While maintaining the temperature just below about 10° C., the clear solution was filled into aluminum tubes. When the solution temperature equilibrated to room temperature, it transformed into a clear gel.

The three examples listed below are compositions according to the invention previously noted. They are all combinations of Ketamine HCl and Gabapentin. They all share the trademarked name "Neurocreme".

Example 1

Neurocreme 15%—100 g Example Size

| Component | Weight | Weight % |
| --- | --- | --- |
| Ketamine HCl | 15 g | 15% |
| Gabapentin | 6 g | 6% |
| Water (purified) | 7.25 ml | 7.25% |
| Lipoderm Base | 70.75 g | 70.75% |
| Krisgel | .89 ml | 1% |

Example 2

Neurocreme 20%—100 g Example Size

| Component | Weight | Weight % |
| --- | --- | --- |
| Ketamine HCl | 20 g | 20% |
| Gabapentin | 6 g | 6% |
| Water (purified) | 10 ml | 10% |
| Lipoderm Base | 61.25 g | 61.25% |
| Krisgel | 2.5 ml | 2.75% |

Example 3

Neurocreme 25%—100 g Example Size

| Component | Weight | Weight % |
| --- | --- | --- |
| Ketamine HCl | 25 g | 25% |
| Gabapentin | 6 g | 6% |
| Water (purified) | 16 ml | 16% |
| Lipoderm Base | 50.25 g | 50.25% |
| Krisgel | 2.5 ml | 2.75% |

Example 4

Neurocreme 30%—100 g Example Size

| Component | Weight | Weight % |
| --- | --- | --- |
| Ketamine HCl | 30 g | 30% |
| Gabapentin | 6 g | 6% |
| Water (purified) | 22 ml | 22% |
| Lipoderm Base | 50.25 g | 40.25% |
| Krisgel | 2.5 ml | 2.75% |

Administration

The compositions described herein are applied two ways via massage: (1) directly to the pain site or appropriate ganglion and (2) into the appropriate dermatome on the spine.

Plan 1 was normally used first, especially if the pain locus is below the patient's waist line (due to reduced systemic circulation of the agents.) The patient is instructed to find the most precise area of pain—if possible—by using a blunt, pointed object (i.e., fingertip, pen tip, etc.) By use of a "checkerboard pattern" search, many times the pain locus is discovered. For example, a foot pain locus may be found by pressing a fingertip on one side of the ankle for approximately 2 seconds then moving the fingertip an inch towards the other side of the ankle. This pressure is repeated "checkerboard style" (across and downward) until the entire foot—top and bottom—has been covered. The patient takes note of what area(s) hurt most and then treats the area(s) with ½ gram or 1 gram of cream at each pain site. If a precise locus cannot be found, then a 1 gram dose to the ganglion located ¾ inch below and ¾ inch behind the inside anklebone will suffice. This ganglion is responsible for innervation of the foot via the L-4, L-5, S-1, and S-2 dermatomes. Other ganglia may be used similarly for pain loci at other anatomical sites. An anesthesiologist—or a medical professional with a thorough understanding of human anatomy—should be consulted for the most appropriate ganglion (or ganglia) to be used.

Plan 2 was used when there is insufficient analgesia provided by Plan 1. Plan 2 requires massage of the cream into the appropriate dermatome on the spinal column. The patient is shown where the correct dermatome application site (on the spine) is for the painful area described by the patient. For example, a foot pain locus requires cream application to the L-4, L-5, S-1, and S-2 vertebrae on the spine.

How much cream to apply depends on (1) the pain site and (2) pain severity. The patient is instructed to use Plan 1 first. During the counseling session, the patient learns to (1) find the pain using the "checkerboard technique" described above and (2) prepare the skin for application by warming the site with a very warm, slightly moist cloth. A minimum dose—usually between ½ to 1 gram—is suggested as a starting dose. A (1-gram+½ gram) dosing spoon is given to the patient for accurate measure. The patient is instructed to use this starting dose 3 times daily for 3 days unless side effects appear. If that happens, the patient is counseled to immediately cease the applications and call his/her doctor. After the 3 day period—and if no sign of analgesia nor side effects—the dose may be increased by ½ gram increments daily. For example, if a 1-gram dose to the site did not relieve the pain during the first 3 days, then the dose would be increased by ½ gram per application on day 4. If the pain was still not managed, the dose would be increased by another ½ gram dose on day 5. The dose total at that point would be 2 grams per application. This sequence would be repeated until (1) the pain is managed or (2) side effects begin. Note: Side effects at any time are the limiting factor for dosing.

If Plan 1 does not provide sufficient analgesia within 7 days of the first application, then the patient is instructed to initiate Plan 2. Application to this area is explained above. Because the area is above the belt line, the patient is told that there is an increased risk of side effects. A 1-gram dose at the correct dermatome is started with the proviso that the dose may be adjusted down or up after a 3 day dosing period. This is similar to Plan 1.

Dosing frequency is dependent on the cream's duration of action. Duration of action varies from patient to patient. Normally, the cream is applied 3 times daily, but more frequent—or less frequent—applications are possible. Again, the limiting factor is side effects. Hence, if no side effects, then multiple daily applications are OK. The cream is a pain management "tool". As such, the cream may be used as often as necessary (subject to side effects.)

Objectives and Advantages

Pain management is one objective of the compositions and methods described herein. The methods and compositions described herein can ameliorate neuropathic pain in patients. The compositions and methods described herein have the following advantages: (1) Surveys have shown that >75% of patients using the compositions described herein have managed their neuropathic pain with at least one embodiment described herein; (2) the compositions described herein are effective against a wide variety of sympathetically mediated pain (SMP) sources—including various neuropathies, low back pain, sciatica, and post-spinal surgery pain; (3) the doses needed to control neuropathic pain are relatively small (see survey, Table 1); (4) dose volumes are also small—a distinct application advantage; (5) patients affected by side effects total less than 22% (includes those who "failed" the cream); (6) the compositions described herein are cosmetically elegant; (7) the compositions described herein are easy to apply because they are readily absorbed by the prepared skin.

TABLE 1

| Number of Patients | Compound Components | Initial Pain Level (10-point scale) | Amount Applied | Application Frequency (Times/day) | Pain Level: One Week | Duration of Action |
|---|---|---|---|---|---|---|
| 1 | Neurocreme 10% | 8 | 1.5 grams | 2.8 | 7 | 4 hours |
| 20 | Neurocreme 15% | 7.2 | 1.6 grams | 2.8 | 3.75 | 3.8 |
| 22 | Neurocreme 20% | 7.9 | 1.4 grams | 4.5 | 3.35 | 4.9 |
| 1 | Neurocreme 25% | 10 | 3 grams | 2 | 2 | X |

Table 1 above describes the most commonly used varieties of the compositions described herein. A subjective 10-point pain scale was used by the patients at baseline and at 7 days to describe their pain. A "1" essentially meant no pain. A "10" described very severe pain—the kind that leaves one in agony. The amount applied was judged by the number of 1 gram-½ gram dispensing spoons used per application. There was tremendous Application Frequency variability. Application times ranged from once a day, every other day to 2, 3, 4, 5 and 6 times daily, or as needed.

Onset of analgesia for all four composition varieties share the same time period. These times varied from a half hour to over 72 hours. The onset times may differ from patient to patient.

Compound #1 (Example 1) achieved a pain reduction of 3.2 points=44% pain reduction. In the survey, 20 people used the 15% strength PLO-based (pluronic-lecithin organogel) transdermal gel but 3 reported treatment failure. This represents a success rate of 84%. 19 patients who used this formulation represent a statistically small sample. This compound was applied to patients with degenerative disc disease, diabetic peripheral neuropathy, fibromyalgia, lower pack pain, myelitis—legs/feet, P/S neuropathy and post-herpetic neuralgia.

Compound #2 (Example 2) achieved a pain reduction of 3.4 points=a 43% pain reduction. More people (#22) have used the 20% strength of the compositions described herein than any other formulation. There were 5 reported failures. This compound was applied to patients with sciatica, spinal stenosis, rheumatoid arthritis, post amputation, polyneuropathy, occipital neuropathy in the legs/feet and the hands, and post-herpetic neuralgia.

Compound #3 (Example 3) achieved a pain reduction of 8 points with one patient, and thus=a 80% pain reduction for a patient with diabetic neuropathy.

The 10% ketamine compound was applied to a patient with lower back pain with minor reduction in pain.

The small sample size is representative but not indicative of the results of other patients. It is likely but not necessarily that greater amount of the NMDA antagonist may increase the amount of pain reduction and/or decrease the reported failures (e.g., via non-analgesia, or side effects).

Pain Reduction

A survey was provided to over 800 patients provided with various ketamine topical formulations combined with other compounds, using PLO or Lipoderm as the transdermal base. For all diagnoses, greater analgesia was achieved with ketamine concentrations greater than or equal to 15%, with best results from 20% or greater. Results show that the various topical formulations were efficacious in relieving pain in 643 of 824 diagnoses (78%). Most initial treatment failures were shown to be due to insufficient analgesia or side effects. The patients were treated for diabetic peripheral neuropathy, low back pain, polyneuropathy in the hands and feet, post-herpetic neuralgia, sciatica, CRPS/RSD, post-surgical neuropathy, and miscellaneous neuropathies including fibromyalgia.

All cited references including publications and patent documents cited in this specification are herein incorporated by reference in their entireties as if each individual publication or patent application were specifically and individually indicated to be incorporated by reference. Although the foregoing methods and compositions have been described in some detail by way of illustration and example for purposes of clarity of understanding, it will be readily apparent to those of ordinary skill in the art in light of the teachings of these methods and compositions that certain changes and modifications may be made thereto without departing from the spirit or scope of the appended claims. The present invention is not to be limited in scope by the specific embodiments disclosed in the examples, which are intended as illustrations of a few aspects of the invention, and any embodiments that are functionally equivalent are within the scope of this invention. Indeed, various modifications of the invention in addition to those shown and described herein will become apparent to those skilled in the art and are intended to fall within the scope of the appended claims.

What is claimed is:

1. A topical composition for the treatment of peripheral neuropathy comprising a therapeutically effective amount of 10% or greater of ketamine and only one additional active compound consisting of 10% or less of gabapentin wherein the composition is formulated in a pharmaceutically acceptable carrier for topical administration, and wherein the additional active ingredient potentiates the activity of ketamine.

2. The topical composition of claim 1, wherein the composition consists essentially of ketamine and gabapentin in a pharmaceutically acceptable carrier for topical administration.

3. The topical composition of claim 1, wherein said topical composition comprises 15% or greater of ketamine.

4. The topical composition of claim 1, wherein said topical composition comprises 20% or greater of ketamine.

5. The topical composition of claim 1, wherein said topical composition comprises less than 10% gabapentin.

6. The topical composition of claim 1, wherein said topical composition comprises about 20% ketamine and about 3% gabapentin.

7. The topical composition of claim 1, wherein said topical composition comprises about 15% ketamine and about 3% gabapentin.

8. A topical composition comprising pharmaceutically active ingredients and carrier ingredients, wherein the pharmaceutically active ingredients consist essentially of at least 10% ketamine and not more than 10% gabapentin, as the only active ingredients and wherein the composition is formulated for topical administration and wherein the additional active ingredient potentiates the activity of ketamine.

9. The topical composition of claim 8, wherein the pharmaceutically active ingredients have at least 15% ketamine.

10. The topical composition of claim 8, wherein the pharmaceutically active ingredients have at least 20% ketamine.

11. The topical composition of claim 8, wherein the pharmaceutically active ingredients consist of 20% ketamine and 3% gabapentin.

12. The topical composition of claim 8, wherein the pharmaceutically active ingredients consist of 15% ketamine and 3% gabapentin.

13. A method for treating a subject suffering from diabetic neuropathy, said method comprising topically administering an effective amount of a topical composition of claim 1.

14. The method of claim 13, wherein the topical composition comprises 15% or greater of ketamine.

15. The method of claim 14, wherein the topical composition comprises about 3% gabapentin.

* * * * *